United States Patent [19]
Goldenberg et al.

[11] Patent Number: 5,629,184
[45] Date of Patent: May 13, 1997

[54] CATIONIC COPOLYMERS OF VINYLAMINE AND VINYL ALCOHOL FOR THE DELIVERY OF OLIGONUCLEOTIDES

[75] Inventors: Merrill S. Goldenberg; Alice C. Beekman, both of Thousand Oaks, Calif.

[73] Assignee: Amgen Inc., Thousand Oaks, Calif.

[21] Appl. No.: 378,301

[22] Filed: Jan. 25, 1995

[51] Int. Cl.⁶ .................................................. C12N 15/00
[52] U.S. Cl. ........................ 435/172.3; 424/78; 514/44
[58] Field of Search ....................... 424/78.01, 78.08; 514/44; 435/172.3

[56] References Cited

U.S. PATENT DOCUMENTS

| | | | |
|---|---|---|---|
| 4,713,236 | 12/1987 | Hoover et al. | 526/310 |
| 5,194,492 | 3/1993 | Pinschmidt, Jr. et al. | 525/60 |
| 5,250,023 | 10/1993 | Lee et al. | 604/20 |
| 5,281,307 | 1/1994 | Smigo et al. | 162/164.3 |
| 5,387,641 | 2/1995 | Yeung et al. | 524/557 |

*Primary Examiner*—Peter F. Kulkosky
*Attorney, Agent, or Firm*—Craig A. Crandall; Steven M. Odre; Ron K. Levy

[57] ABSTRACT

The present invention relates to an improved method for the cytoplasmic delivery of oligonucleotides using cationic copolymers based on vinyl alcohol with low levels of vinyl amine (PVAVAMs). Improved compositions for use in such method are also provided.

13 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

GCTGTGGGGC GGCTCCTG     18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

CGCCGTCGCG GCGGTTGG     18

CATIONIC COPOLYMERS OF VINYLAMINE AND VINYL ALCOHOL FOR THE DELIVERY OF OLIGONUCLEOTIDES

The present invention relates generally to an improved method for the cytoplasmic delivery of polyanions. More particularly, the invention relates to an improved method for the cytoplasmic delivery of oligonucleotides and to improved compositions for use in such method.

BACKGROUND OF THE INVENTION

Oligonucleotides are powerful modulators of cell properties at the DNA or RNA level. Oligonucleotides may be designed to base-pair to a specific segment of DNA (triplex-forming oligonucleotides) or RNA (antisense oligonucleotides), and, after binding to the desired target nucleic acid, affect transcription and/or translation with predictable downstream biochemical and functional consequences, i.e., they inhibit gene expression. The exact mechanism by which oligonucleotides act to inhibit gene expression is still not known in all cases. Recent advances in organic synthesis and purification techniques have facilitated practicability for design and synthesis of oligonucleotides.

Because oligonucleotides are designed to bind specifically to matching sequences, they possess a high degree of specificity, and have vast potential therapeutic applications. For example, the two most common problems associated with the use of anticancer and antiviral agents are drug resistance and unacceptable levels of toxicity. These are potentially overcome by the use of oligonucleotides having high degree of specificity because: (1) genes that do not contain the target sequence are theoretically unaffected by the oligonucleotides, thereby reducing the probability of toxicity; and (2) only a point mutation within the oligonucleotide binding site, not outside, can lead to drug resistance. Therefore, oligonucleotides are thought to represent a class of powerful anticancer and antiviral agents.

Inefficient intracellular bioavailability of oligonucleotides, i.e., the amount of intact oligonucleotide that is available in a form that can interact with its intended target, has been a major obstacle in the development of oligonucleotides as therapeutic agents. Key factors contributing to inefficient intracellular bioavailability are poor stability, nonspecific binding, and poor cellular and tissue uptake.

Extensive work has been done to design derivatives of oligonucleotides having improved properties. Modifications in the nucleoside, sugar backbone, terminus, or stereochemistry comprise the four main categories of derivatization; see Uhlmann and Peyman, *Chem. Rev.*, 90: 543–584 (1990). In addition, several delivery strategies that may circumvent some of these problems are being explored; see Akhtar and Juliano, *Trends in Cell Biology*, 2: 139–144 (1992) and references cited therein.

The mechanism of cellular uptake is not completely understood. For example, it is unclear whether oligonucleotide uptake occurs via a previously described transport mechanism in the cell membrane, or by a unique pathway; see Wu-Pong, *Pharmaceutical Tech.*, pgs 102–112 (October 1994). In addition, it appears that the uptake mechanism may be cell-type and/or oligonucleotide-type dependent. Id. Current evidence indicates that oligonucleotides predominantly enter cells by endocytosis. Endocytosis is typically classified as receptor-mediated endocytosis (RME), adsorptive endocytosis (AE), and fluid-phase endocytosis (FPE).

Following endocytosis, the oligonucleotides must escape from endosomal compartments in order to exert their effects in the nucleus or cytoplasm. The precise mechanism and extent of oligonucleotide transfer from endosomes to cytoplasm and/or nuclear targets remains uncertain. Possible mechanisms are simple diffusion, transient membrane destabilization, or simple leakage during a fusion event in which endosomes fuse with other vesicles such as lysosomes. In order for oligonucleotides taken up by endocytosis to be useful, their efflux from the endosomal compartments must be improved.

Various synthetic methods have been proposed in the literature to improve intracellular bioavailability. One reported approach is the covalent attachment of specific cell receptor ligands to initiate cellular uptake by receptor-mediated endocytosis; see Vestweber and Schatz, *Nature*, 338: 170–172 (1989). Covalent modification of oligonucleotides generally involves the use of polycations and is a laborious procedure which requires a separate synthesis and purification for each oligonucleotide tested. Polycations such as poly-L-lysine have been reported to have been used in gene transfection studies; see Felgner, *Advanced Drug Delivery Reviews*, 5: 163–187 (1990). However, unlike gene tranfection, where relatively few copies of DNA are needed, use of oligonucleotides as a therapeutic agent would require high levels of DNA, and covalent modification using polycations such as poly-L-lysine may be toxic to the cells.

The most popular approach currently being investigated is the use of phospholipid vesicles (liposomes) to deliver oligonucleotides to cells; see Akhtar et al., *Nucleic Acids Res.*, 19: 5551–5559 (1991). In addition to protecting oligonucleotides from enzymatic degradation, liposomes offer the potential to control and sustain their release. Id. Efflux of oligonucleotides from liposomes appears to be slow and sustainable over a period of several days, suggesting that they may be useful in delivering oligonucleotides against targets that have a slow turnover. Id. However, as was the case with other polycations, cationic lipids and liposomes (e.g. Lipofectin®) are generally toxic to the cells and inefficient in their DNA delivery in the presence of serum; see Leonetti et al., *P.N.A.S. USA*, 87: 2448–2451 (1990).

There have been extensive reports on the synthesis and use of copolymers, based on vinyl alcohol with varying levels of vinylamine, in the paper industry; see European Patent Publication 337310; European Patent Publication 339371; European Patent Publication 617166; U.S. Pat. Nos. 4,774,285, 4,880,497, 4,978,427 and 5,270,379, and as flocculants; see U.S. Pat. No. 3,715,336. There are no known reports to date relating to the use of vinyl alcohol/vinylamine copolymers for cellular therapy.

The oligonucleotide modifications and/or delivery systems described in the literature have led to improved efficiency of oligonucleotide cellular uptake; however, they have yet to allow the full potential of oligonucleotide technology to be realized. Therefore, there exists the need to develop improved methods for increasing the intracellular bioavailability of oligonucleotides. It is an object of the present invention to provide such methods. It is a further object of the invention to provide compositions for use in such methods.

SUMMARY OF THE INVENTION

The present invention relates generally to improved compositions and methods for the cytoplasmic delivery of polyanions. More particularly, the invention relates to an improved methods for the cytoplasmic delivery of oligonucleotides and to improved compositions for use in such methods. The present invention grew out of studies in which copolymers based on vinyl alcohol and vinyl amine (PVAVAMs) were used to deliver polyanions (here, oligonucleotides) to cells. Surprisingly, the PVAVAMs provide an efficient system to achieve nuclear delivery of oligonucleotides in cells, in the presence of serum and with low toxicity.

The compositions of the present invention comprise combination of PVAVAMs, at varying mole % vinyl amine content, to an oligonucleotide, such that the molar ratio of polymerized vinyl amine to oligonucleotide anion units is between 0.1–100. Preferably, the molar ratio is 0.2–30. Most preferably, the molar ratio is 0.2–15.

The methods of the present invention comprise administration of the PVAVAM/oligonucleotide compositions to the cells such that the oligonucleotide is transported into the cells.

The PVAVAMs utilized by the methods of the present invention are prepared using hydrophobic and hydrophilic polymerizable vinylic monomers and have from 0.5–75 mole % vinyl amine content. Preferably, the PVAVAMs are prepared using vinyl acetate/vinyl formamide and vinyl alcohol/vinyl formamide precursor polymers and have from 4–20 mole % vinyl amine content. Most preferably, the PVAVAM has from 6–15 mole % vinyl amine content.

The polyanions contemplated for use in the methods of the present invention are generally macromolecular in size. However, also encompassed are low molecular weight materials which have the ability to complex to PVAVAMs, i.e., containing regions of anionic character (anion units). Preferably, the polyanion is a protein, polypeptide, oligonucleotide, polynucleotide, or drug. In a preferred embodiment, the polyanion is an antisense oligonucleotide.

DETAILED DESCRIPTION OF THE INVENTION

Copolymers of the present invention are comprised of vinyl alcohol (VA), and vinylamine (VAM), of the general formula I,

—(CH$_2$—HCOH—)x—(CH$_2$—HCNR1R2R3—)y—Az—   I.

where

R1, R2 and R3 are independently hydrogen, lower alkyl or 2-hydroxyalkyl, or R1=R2=hydrogen, lower alkyl or 2-hydroxyalkyl and R3 is a lone pair electron A is the residual of a vinylic monomer x, y, and z are integers, representing the number of incorporated monomer and where x+y+z=100

For purposes of describing the present invention, the copolymers of formula I will be referred to as "PVAVAMs". The phrase "residual of a vinyl monomer" is defined as the monomer unit after polymerization, and it should be noted that the final PVAVAM may contain minor amounts of residual units and initiator fragments.

In the PVAVAMs of the present invention, it is preferred that R1=R2=R3=hydrogen or R1=R2=hydrogen and R3 is a lone pair electron, and further, that x=25–99.5 mole %, y=0.5–75 mole %, and z<50 mole %. More preferably, x=80–96 mole %, y=4–20 mole %, and z≦16 mole %. It is most preferred that x=87–94 mole %, y=6–13 mole %, and z≦10 mole %. For purposes of the present invention, "mole %" is defined as the percentage of the total mole units in the polymer.

In general, the process of synthesizing the PVAVAM target polymers of the present invention consists of performing a series of hydrolyses on a precursor polymer. The precursor polymer is formed by copolymerizing a vinyl alcohol precursor monomer such as vinyl acetate (VAc) and a vinyl amine precursor monomer such as N-vinyl formamide (NVF). The free radical polymerization is performed by methods well known in the art; see, for example, *Vinyl and Related Polymers* by C. E. Schildknecht, 1952, published by John Wiley & Sons, Inc. The acetate is hydrolyzed with a catalytic level (~3 mole %) of base, such as methanolic NaOH and the formamide is hydrolyzed with a slightly greater than stoichiometric level of either HCl or NaOH. Such polymerization processes are described in detail in the literature; see European Patent Publication 0339371 A2 (Pinschmidt and Lai),and references cited therein. One skilled in the art will recognize variations in the method of preparation of the present polymers.

Suitable vinylic monomers for polymerization include conventional hydrophobic and hydrophilic monomers. Suitable hydrophobic monomers include, without limitation, C$_1$ to C$_{18}$ alkyl acrylates and methacrylates, C$_3$ to C$_{18}$ alkylacrylamides and methacrylamides, acrylonitrile, methacrylonitrile, vinyl C$_1$ to C$_{18}$ alkanoates, C$_2$ to C$_{18}$ alkenes, C$_2$ to C$_{18}$ haloalkenes, styrene, C$_1$ to C$_6$ alkyl styrenes, vinyl alkyl ethers wherein the alkyl portion has 1 to 6 carbon atoms, C$_3$ to C$_{12}$ perfluoroalkylethyl thiocarbonylaminoethyl acrylates and methacrylates, C$_3$–C$_{12}$ flouroalkyl acrylates and methacrylates, acryloxy and methacrloxy alkyl siloxanes, N-vinyl carbazole, C$_1$–C$_{12}$ alkyl esters of maleic, fumaric, itaconic, and mesaconic acids and the like.

Examples of suitable hydrophobic monomers include methyl acrylate, ethyl acrylate, propyl acrylate, isopropyl acrylate, cyclohexyl acrylate, 2-ethylhexyl acrylate, methyl methacrylate, propyl methacrylate, vinyl acetate, vinyl propionate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, 3-methacryloxypropylpentamethyldisiloxane, and bis (methacryloxypropyl)tetramethyldisiloxane.

Suitable hydrophilic monomers include, without limitation, hydroxy substituted lower alkyl acrylates and methacrylates, N-vinyl formamide, acrylamide, methacrylamide, C$_1$–C$_2$ lower alkyl acrylamide and methacrylamide, ethoxylated acrylates and methacrylates, hydroxy substituted lower alkyl acrylamide and methacrylamide, hydroxy substituted lower alkyl vinyl ethers, sodium styrene sulfonate, 2-acrylamido-2-methylpropanesulfonic acid, N-vinylpyrrole, N-vinyl succinimide, N-vinyl pyrrolidone, 2- and 4-vinyl pyridine, acrylic acid, methacrylic acid, amino (including quaternary ammonium), monoloweralkylamino- or diloweralkylamino-lower alkyl acrylates or methacrylates, allyl alcohol, and the like.

The copolymers of the present invention can also be modified to a minor degree with anhydrides, epoxides, isocyanates, reactive carbonyls, haloalkylcarbonyls, esters, aziridines, Michael acceptors, acid chlorides, lower alkyl halides and the like. Examples of modifying reagents include, succinic anhydride, maleic anhydride, citraconic anhydride, iodoacetic acid, polyoxyethylene or carbohydrate derivatives such as active esters, maleimides, vinyl sulphones and the like.

The lengths of the oligonucleotides of the present invention may vary to some degree, but will generally be from about 10 to about 30 nucleotides in length. It is preferred for reasons of commercial practicability that the oligonucleotide be from about 14 to about 20 bases long, as longer oligonucleotides within the 10 to 30 nucleotide range may hybridize nonspecifically to other non-target sequences if the oligonucleotide is too long (i.e., substantially longer than 20 nucleotides).

The compositions encompassed by the present invention comprise PVAVAMS combined with antisense oligonucleotides. The nature of the interaction is unknown, but it is presumably electrostatic. The compositions can be characterized as follows: the PVAVAM serves as a "carrier" and the oligonucleotide as a "passenger", and the PVAVAM/oligonucleotide combination is a "noncovalent carrier/passenger complex or system." The fraction of PVAVAM to oligonucleotide in the compositions is based on amine containing units to phosphate units and is 0.001 to 1000, preferably 0.01–500, more preferably 0.1–100, more preferably 0.2–30, and most preferably 2–15.

It is contemplated by the present invention that the PVAVAMs of the present invention may be used for delivery of proteins (e.g., growth factors, cytokines, immunoglobulins, hormones), polypeptides, polynucleotides, oligonucleotides, drugs and other therapeutic agents to cells. As such, the compositions of the present invention may provide for methods of use in the clinical setting, e.g. inhibition of smooth muscle cell proliferation, treatment of cell proliferation disorders, inflammation, and treatment of viral disease. Mixture of the compositions of the present invention with a pharmaceutically acceptable carrier, diluent, preservative, solublizer, adjuvants and/or emulsifier; see Remington's Pharmaceutical Sciences, 18th Edition (1990, Mack Publishing Co., Easton, Pa. 18042) pages 1435–1712 which are herein incorporated by reference, is also contemplated.

Example 1 below demonstrate the methods of preparation of the components of the compositions of the present invention. Example 2 demonstrates the preparation and use of the present compositions (and methods). As shown by cellular uptake studies, the present PVAVAM compositions facilitate cellular uptake of antisense oligonucleotides.

EXAMPLE 1

This example demonstrates (i) synthesis of oligonucleotides, (ii) fluorescent labeling of the oligonucleotides for use as markers in the cellular uptake studies in Example 2 and (iii) preparation of various copolymers.

I. Synthesis of the oligonucleotides

The oligonucleotides used in the following examples were synthesized using an Applied Biosystems Inc. (Foster City, Calif.) Model 394 DNA synthesizer. Phosphorothioate modified linkages were introduced by oxidizing the phosphite linkage formed during oligonucleotides synthesis with $^3$H-1,2-benzodithiole-3-1,1-dioxide (Beaucage reagent, Glen Research, Sterling Va.) instead of the standard iodine oxidation. The four common nucleoside phosphoramidites (i.e., adenine, thymine, guanine and cytosine) and deoxyinosine phosphoramidite were purchased from Applied Biosystems Inc. All unmodified phosphodiester and modified thioate-containing oligonucleotides were deprotected by treatment with concentrated ammonia at 55° C. for 12 hours. The oligonucleotides were purified by gel exclusion chromatography and ethanol precipitation and lyophilized to dryness.

The oligonucleotides used in the following examples were fully modified with phosphorothioate linkages and are shown below:

OLIGO 1 GCT GTG GGG CGG CTC CTG (SEQ ID NO:1)
OLIGO 2 CGC CGT CGC GGC GGT TGG (SEQ ID NO:2)

Oligonucleotides 1 is an 18-mer phosphorothioate-modified oligonucleotide which has a similar base composition as the human anti-c-myb antisense sequence. Oligonucleotide 2 is an 18-mer phosphorothioate-modified oligonucleotide having no known antisense target.

II. Labeling of the oligonucleotides

Fluorescein was incorporated into the oligonucleotides at the 5'-terminus using a fluorescein amidite purchased from Glen Research (Sterling Va.) and used according to manufacturers specifications.

III. Copolymer preparation

The text below illustrates the preparation and characterization of PVAVAM target copolymers prepared from the hydrolysis of vinyl acetate/vinyl formamide and vinyl alcohol/vinyl formamide precursor polymers. The PVAVAMs prepared had varying vinyl amine content. The vinyl amine content of the PVAVAMs was determined by potentiometric titration.

1. Preparation of the PVAVAMS

The preparations will be illustrated in a three step procedure: Step 1 involves the synthesis of the vinyl acetate/vinyl formamide precursor polymer; Step 2 involves the synthesis of the vinyl alcohol/vinyl formamide precursor polymer; and Step 3 involves the synthesis of the PVAVAM target copolymer. The PVAVAMs prepared had varying vinyl amine content (ratio of N-vinyl formamide to vinyl acetate reflects the variation of amine to alcohol content).

2. Characterization of PVAVAMs

Vinylamine content of the PVAVAM was measured by potentiometric titration of a weighed amount of polymer (~0.5 g) dissolved in 100 mL water. When the PVAVAM was in the form of a free base (e.g., when the aqueous base hydrolysis of the formamide had been used), the initial pH was generally above 10, and was brought to ~1.99 with HCl, then raised to ~12.01 with NaOH. For hydrochloride salts generated by the nonaqueous acid hydrolysis of the formamide, the initial pH of 4 or less was raised to ~12.01 with NaOH, then dropped to ~1.99 with HCl. The curves of both titrations for each solution were compared and showed good agreement for the response of pH to mEq of titrant. After examination of a plot of ΔpH/ΔmEq as well as the titration curve itself, the mEq of amine was determined and the weight percent and mole percent of amine calculated.

Preparation A

Step 1.

The reactor (500 mL 4 neck jacketed flask equipped with a teflon-bladed overhead stirrer, condenser, thermometer and teflon tube feed lines) contains 1.42 g N-vinyl formamide (NVF), 84.28 g vinyl acetate (VAc) (Polysciences) and 67 g methanol. The feed contains 5.33 g NVF and 36.55 g VAc. The polymerization is performed at 60° C. under nitrogen using 0.51 g tert-butyl peroxyneodecanoate (AKZO Chemicals Inc.). The feed is delivered at a rate of approximately 7 to 15 mL/h over a 3 hour period and methanol is added periodically to restore volume. The polymerization is halted by the addition of 14.8 mg of methyl ether hydroquinone (MEHQ) (Polysciences). Excess VAc is removed by azeotropic distillation with methanol.

Step 2.

VAc/NVF polymer (29 g) is rapidly mixed with 1.6 g 50% NaOH(0.02 moles) in 150 mL MeOH. The hydrolysis is performed at 40° C. for 30 minutes. The resultant VA/NVF polymer precipitate is washed with MeOH and dried at 60° C. in vacuo. The yield is 11.3 g.

Step 3.

VA/NVF polymer (8 g) is suspended in 72 mL methanol and mixed with 1.32 mL 12N HCl (0.0158 moles) in 16 mL methanol. The hydrolysis is performed at 60° C. for 2 hours. The resultant VA/VAM polymer is washed with methanol and dried at 50° C. in vacuo. The yield is 8.08 g, and the amine content is 4.6 mole %.

Preparation B

This polymer is prepared in a similar manner as Preparation A with the following modifications to Step 1: the reactor contains 3.55 g NVF, 81.7 g VAc, 100 mL methanol and 0.49 g tert-butyl peroxyneodecanoate; the feed contains 12.5 g NVF and 27.9 g VAc; an additional 0.263 g of tert-butyl peroxyneodecanoate is added 2½ hours after the first addition. In addition, methanol is periodically added to restore volume. The polymerization is halted by the addition of 15.7 mg of MEHQ after 4 hours of polymerization and at this point 8.5 mL of feed is remaining.

Step 2.

VAc/NVF precursor polymer (41 g) in 230 mL methanol is rapidly mixed with 1.04 g of 50% NaOH and hydrolyzed at 40° C. for 30 minutes. The VA/NVF polymer precipitate is washed with methanol and dried at 45° C. in vacuo. The yield is 23.64 g.

Step 3.

The VA/NVF polymer (10 g) is dissolved in 40 g $H_2O$, 2.515 g of 50% NaOH added and the mixture heated at 80° C. for 8 hours. The product is exhaustively dialyzed (Spectrapor, 3500 MWCO) against deionized water and 80% of this solution is lyophilized to a cotton-like white material. The yield of the resultant VA/VAM polymer is 5.67 g, and the amine content is 13.9 mole %.

Preparation C

This polymer is prepared in a similar manner as Preparation A with the following modifications to Step 1: the reactor contains 2.48 g NVF, 83 g VAc, 120 mL methanol and 0.51 g tert-butyl peroxyneodecanoate; the feed contains 9.12 g NVF and 31.95 g VAc. Methanol is added periodically to maintain the volume. An additional 0.29 g tert-butyl peroxyneodecanoate is added 2 hours after the initial addition. The polymerization is halted by the addition of 20 mg of MEHQ after 3 hours 40 minutes of polymerization.

Step 2.

The VAc/NVF polymer (12.5% solids) in approximately 200 mL methanol is rapidly mixed with 0.759 g of 50% NaOH and heated at 40° C. for 25 minutes. The VA/NVF polymer precipitate is washed with methanol and dried at 45° C. in vacuo. The yield is 14.8 g.

Step 3.

The VA/NVF polymer (13.0 g) is suspended in 117 mL methanol. To this is dropwise added 3.02 mL of 12N HCl (0.0362 mole) in 26 mL methanol. The mixture is heated at 60° C. for 2 hours. After washing and lyophilizing, the yield of the resultant VA/VAM is 8.5 g, and the amine content is 8.6 mole %.

Preparation D

This polymer is prepared in a similar manner as Preparation B with the following modifications to Step 1: the reactor contains 3.55 g NVF, 81.70 g VAc, 100 mL methanol and 0.49 g tert-butyl peroxyneodecanoate; the feed contains 12.55 g NVF and 27.90 g VAc. In addition, methanol is periodically added to restore volume. The polymerization is halted by the addition of 21.6 mg of MEHQ after 4½ hours of polymerization.

Step 2.

The VAc/NVF polymer (approximately 34 g) in approximately 200 mL methanol is rapidly mixed with 0.847 g of 50% NaOH (0.0106 mole) at 40° C. for 25 minutes. The polymer is washed with methanol and dried at 45° C. in vacuo. The yield of VA/NVF polymer is 22.7 g.

Step 3.

The VA/NVF polymer (20 g) is mixed with 80 g water and 5.0 g of 50% NaOH and heated at 80° C. for 6 hours. After dialyzing and lyophilizing, the yield of the resultant VA/VAM is 12.38 g, and the amine content was 10.4 mole %.

Preparation E

This polymer is prepared in a similar manner as Preparation A with the following modifications to Step 1: the reactor contains 3.05 g NVF, 82.3 g VAc, 100 mL methanol and 0.6 g tert-butyl peroxyneodecanoate; the feed contains 11.08 g NVF and 29.58 g VAc. Methanol is added periodically to maintain the volume. The polymerization is halted by the addition of 19.4 mg of MEHQ after 4¼ hours of polymerization.

Step 2.

The VAc/NVF polymer (approximately 52 g) in 250 mL methanol is rapidly mixed with 1.28 g of 50% NaOH (0.016 mole) at 40° C. for 25 minutes. The polymer is washed with methanol and dried at 45° C. in vacuo. The yield of VA/NVF polymer is 29.97 g.

Step 3.

The VA/NVF polymer (18 g) is suspended in 180 mL methanol. To this is dropwise added 4.2 mL of 12N HCl in 36 mL methanol. The mixture is heated at 60° C. for 2 hours. After filtering, washing and drying at 50° C. in vacuo, the material is dissolved in ~4 liters of water and then half of the material is lyophilized. The yield of the resultant VA/VAM is 6 g, and the amine content is 10.4 mole %.

Preparation F

This polymer is prepared in a similar manner as Preparation C with the following modifications to Step 1 to reduce the molecular weight as compared to Preparation C: the reactor contains 0.62 g NVF, 20.87 g VAc, 169 mL methanol and 0.5 g tert-butyl peroxyneodecanoate; the feed contains 2.28 g NVF, 7.99 g VAc and 32.7 mL of methanol. Methanol is added periodically to maintain the volume. The polymerization is halted by the addition of 23 mg of MEHQ after 4 hours of polymerization.

Step 2.

The VAc/NVF polymer (approximately 17 g) in approximately 108 mL methanol is rapidly mixed with 0.447 g of 50% NaOH (0.056 mole) at 40° C. for approximately 20 hours. The polymer is washed with methanol and dried at 45° C. in vacuo. The yield of VA/NVF polymer is 4.04 g.

Step 3.

The VA/NVF polymer (3.7 g) is suspended in 33.3 mL methanol. To this is dropwise added 0.85 mL of 12N HCl in 7.32 mL methanol. The mixture is heated at 60° C. for 2½ hours. After filtering, washing and drying at 50° C. in vacuo, the yield of the resultant VA/VAM is 1.86 g, and the amine content is 8.8 mole %.

Preparation G

This polymer is prepared in a similar manner as Preparation F with the following modifications to Step 1 to reduce the molecular weight as compared to Preparation C: the reactor contains 2.48 g NVF, 83.00 g VAc, 200 mL methanol and 0.51 g tert-butyl peroxyneodecanoate; the feed contains 9.12 g NVF and 31.95 g VAc. Methanol is added periodically to maintain the volume. The polymerization is halted by the addition of 22 mg of MEHQ after 2¾ hours of polymerization. The final volume left in the feed is 14.5 mL.

Step 2.

The VAc/NVF polymer (approximately 47 g) in 225 mL methanol is rapidly mixed with 1.23 g of 50% NaOH at 40°

C. for approximately 30 minutes. The polymer is washed with methanol and dried at 45° C. in vacuo. The yield of VA/NVF polymer is 27.58 g.

Step 3.

The VA/NVF polymer (10 g) is suspended in 90 mL methanol and to this is added 2.3 mL 12N HCl in 20 mL methanol. The mixture is heated at 60° C. for 2 hours. After filtering, washing and drying at 50° C. in vacuo, the yield of the resultant VA/VAM is 8.2 g, and the amine content is 8.6 mole %.

EXAMPLE 2

This example describes the preparation of PVAVAM/ oligonucleotide compositions and cellular uptake experiments using the compositions.

I. Preparation of the compositions

The oligonucleotides used in this example are those described in Example 1. The PVAVAMs used in this example had varying vinyl amine content and were prepared and characterized in a similar manner as those prepared in Example 1. PVAVAM/oligonucleotide compositions were prepared by mixing polymer solution (1–10% w/v in water) and 1 mM fluoresceinated oligonucleotide (18-mer, in water) with medium in 1 mL total volume. In most experiments, minimal medium (DMEM) is used, however, CHO medium with 5% serum can be substituted with similar results. In the design of the treatments, the oligonucleotide concentration was held at 10 µM (180 µM in nucleotide phosphates) and polymer added such that the total polymeric amine level was a given multiple of the phosphates (see Table I). The PVAVAM/oligonucleotide compositions were prepared 25 minutes in advance and warmed in the 37° C., 10% $CO_2$ incubator.

II. Cellular Uotake Experiments

Adherent cultures of CHO D⁻ cells were maintained in 25 mL of medium in T75 tissue culture flasks in a 37° C., 10% $CO_2$ incubator. The culture medium consisted of Dulbecco's Modified Eagle Medium (DMEM, as described in the Gibco catalogue, catalogue #11965-050) supplemented with 5% fetal bovine serum (Hyclone#1905-AA, inactivated by 30 minutes of heat treatment in a 60° C. water bath), 1% of "100×" L-glutamine (Gibco 25030-016), 1% of "100×" HT Supplement (Gibco 11067-014) and 1% of "100×" MEM nonessential amino acids (Gibco 14190-144).

Cells were plated out for experiments at the time of passage, when the cells had reached confluence. Trypsinization was done to harvest the cells from the flask surface. The trypsin solution was a dilution of "10×" trypsin-EDTA (Gibco 15400-021) in Dulbecco's PBS (Gibco 14190-144) such that the final concentration was 1.5× (e.g., 100 mL of the trypsin was mixed with 567 mL of the PBS—this dilution was prepared in advance, sterile filtered, aliquoted in sterile containers and stored at −20° C. The trypsin solution was thawed, warmed and refiltered just before use.) To recover the cells, the medium was aspirated off and any residual medium (which contains trypsin inhibitor) rinsed away with two rapid 8–10 mL rinses of trypsin solution followed by a 5 minute incubation of the cells with 5 mL of trypsin solution. The detached cells were resuspended to make a "5×" concentrate. Subcultures were typically at 1/10 or 1/20 dilution (e.g., for a 25 mL subculture at 1/10, 0.5 mL of cell suspension was used). For the experiments, cells were plated out in 6-well tissue culture plates (Falcon #3046) at 5 mL per well. A 1/10 dilution was generally ready the next day, a 1/20 in two days.

In general cells were 30–50% confluent at the time of the experiment. Treatments were done by aspirating off the old medium and adding the treatment solution containing the PVAVAM/oligonucleotide. The treatment solutions can contain serum. Care was taken not to dry the cells. After the cells had been incubated for one hour, the treatment solutions were aspirated off and the wells were washed 5 times with DMEM, 2 mL per wash, then full medium was added to the wells for the "chase."

The live cells were examined on a NIKON Diaphot inverted microscope with fluorescence attachments and Polaroid camera. A given field was first viewed by phase contrast, then the visible light was dimmed to view the corresponding fluorescent field. Where nuclear uptake was seen, the phase image of the cell was brought back again to assess the health and integrity of the cell. Uptake was scored as follows:

| Score | Fluorescence localization |
|---|---|
| 0 | Little or no cell associated fluorescence |
| 1 | Mainly associated with surface, some endosomal |
| 2 | Heavy, both surface and endosomal |
| 3 | Smooth and diffuse cytoplasmic and throughout cell |
| 4 | Initially surface and endosomal; up to 5% of nuclei stained after a few hours of chase, |
| 5 | Initially surface and endosomal with 10% or less nuclear staining; 30–40% of nuclei stained after a few hours |
| 6 | Initially 80% or more of nuclei tained |
| D | No score, cells disintegrated at beginning of chase |

The results of the uptake experiments are set forth in TABLE 1.

TABLE 1

| Amine Mole % | Molar ratio of y to anion unit | Uptake |
|---|---|---|
| 0 | 0 | 0 |
| ~1 | 9.5–19 | 1 |
| ~3 | 6.8–9.5 | 1 |
| 4.6 | 7.3 | 2 |
| 4.8 | 9.5 | 2 |
| 8.6 | 3.8–7.5 | 5 |
| 8.8 | 9.5 | 5–6 |
| 8.6 | 3.8 | 5 |
| 10.4 | 9.8 | D |
| | 4.9 | 6 |
| 10.4 | 5.3 | 3–4 |
| ~12 | 4.7 | 3–4 |
| 13.9 | 0.46–0.92 | 6 |
| | 1.8 and up | D |
| 100 | 9.4 | D |

This example illustrates that one can achieve improved cellular uptake with substantial nuclear delivery and low toxicity by the use of PVAVAMs. In the absence of PVA-VAM most of the cells are non-fluorescent while in the presence of vinyl amine homopolymer the cells are reduced to fluorescent debris. In general, higher levels of amine lead to cytotoxicity while lower levels lead to an endosomal/ lysosomal distribution. For cytoplasmic or nuclear delivery there is a trend of higher ratio of amine to anion unit at a lower mole % amine in the PVAVAM: for example, at 10.4 mole % amine a preferred amine to anion unit multiple is 4.9 while at 8.8 mole % amine a preferred multiple is 9.5.

Although the invention has been described and illustrated with respect to specific PVAVAM/polyanion compositions and methods, it will be apparent to one of ordinary skill that a variety of related compositions, and cellular delivery methods may exist without departing from the scope of the invention.

What is claimed is:

1. A composition comprising a copolymer of the general formula I, $$-(CH_2-HCOH-)_x-(CH_2-HCNR1R2R3-)_y-(A)_z-\qquad I.$$

where

R1, R2 and R3 are independently hydrogen, lower alkyl or 2-hydroxyalkyl; or R1=R2=hydrogen, lower alkyl or 2-hydroxyalkyl and R3 is a lone pair electron A is a residual unit of a vinylic monomer x, y, and z are integers, representing the number of incorporated monomer and where x+y+z=100 wherein x=25–99.5 mole %, y=0.5–75 mole %, and z<50 mole %, combined with a polynucleotide, wherein the molar ratio of y to anion units is 0.1–100, optionally in a pharmaceutically acceptable carrier, and wherein said composition allows for the cellular uptake of the polynucleotide.

2. A composition according to claim 1, wherein x=80–96 mole %, y=4–20 mole %, and z≦16 mole %.

3. A composition according to claim 1, wherein x=85–94 mole %, y=6–15 mole %, and z≦9 mole %.

4. A composition according to claim 1, 2, or 3, wherein the molar ratio of y to anion units is 0.2–30.

5. A composition according to claim 1, 2, or 3, wherein the molar ratio of y to anion units is 2–15.

6. A composition according to claims 1, 2, or 3, wherein R1=R2=R3=hydrogen, and wherein A is a residual unit of vinyl acetate and vinyl formamide.

7. A composition according to claims 1, 2, or 3, wherein R1=R2=hydrogen, wherein R3 is a lone pair electron, and wherein A is a residual unit of vinyl acetate and vinyl formamide.

8. A composition according to claim 1, wherein said polynucleotide is an oligonucleotide, wherein said oligonucleotide comprises a phosphate backbone.

9. A composition according to claim 8, wherein said oligonucleotide is an antisense oligonucleotide.

10. A composition according to claim 9, wherein the length of said antisense oligonucleotide is from 10 to 30 nucleotides.

11. A composition according to claim 10, wherein the length of said antisense oligonucleotide is 18 nucleotides.

12. A method of effecting cellular uptake of a polynucleotide comprising administration of the composition of claims 1–3 to the cells such that the polynucleotide is transported into the cells.

13. A method of effecting cellular uptake of an oligonucleotide comprising administration of the composition of claims 8–11 to the cells such that the oligonucleotide is transported into the cells.

* * * * *

UNITED STATES PATENT AND TRADEMARK OFFICE
CERTIFICATE OF CORRECTION

PATENT NO. : 5,629,184
DATED : May 13, 1997
INVENTOR(S) : Merrill S. Goldenberg; Alice C. Beekman It is certified that error appears in the above-identified patent and that said Letters Patent is hereby corrected as shown below:

Column 3, line 61; change the "$\leqq$" to --$\leq$--.
Column 3, line 63; change the "$\leqq$" to --$\leq$--
Column 6, line 04; change "Oligonucleotides" to --Oligonucleotide--.
Column 9, line 33; change "Uotake" to --Uptake--.
Colume 11, line 53; change the "$\leqq$" to --$\leq$--.
Colume 11, line 55; change the "$\leqq$" to --$\leq$--.

Signed and Sealed this

Twelfth Day of May, 1998

Attest:

BRUCE LEHMAN

*Attesting Officer*     Commissioner of Patents and Trademarks